(12) United States Patent
Kanaan

(10) Patent No.: US 8,010,380 B2
(45) Date of Patent: Aug. 30, 2011

(54) SYSTEM AND METHOD FOR HEALTHCARE ADVISORY SYSTEM

(75) Inventor: Muzaffer Kanaan, Watertown, MA (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 27 days.

(21) Appl. No.: 11/695,357

(22) Filed: Apr. 2, 2007

(65) Prior Publication Data

US 2008/0243863 A1  Oct. 2, 2008

(51) Int. Cl.
*G06Q 50/00* (2006.01)
*G06Q 10/00* (2006.01)

(52) U.S. Cl. .................. 705/2; 705/3
(58) Field of Classification Search .......... 705/2–3
See application file for complete search history.

(56) References Cited

U.S. PATENT DOCUMENTS

| | | | |
|---|---|---|---|
| 5,752,976 A * | 5/1998 | Duffin et al. | 607/32 |
| 6,031,455 A * | 2/2000 | Grube et al. | 340/539.26 |
| 6,321,158 B1 * | 11/2001 | DeLorme et al. | 701/201 |
| 2002/0013538 A1 * | 1/2002 | Teller | 600/549 |
| 2003/0158465 A1 * | 8/2003 | Galli | 600/300 |
| 2005/0093709 A1 * | 5/2005 | Franco et al. | 340/686.1 |
| 2005/0275530 A1 * | 12/2005 | Kates | 340/539.22 |

OTHER PUBLICATIONS

Editor, Mobile phone text messaging can help young people manage asthma, Sep. 14, 2002, British Medical Journal, 325(7364): 600.*
Munoz-Furlong, Daily Coping Strategies for Patients and Their Families, Pediatrics 2003;111;1654-1661.*
Munoz-Furlong, Daily Coping Strategies for Patients and Their Families, Pediatrics 2003;111 ;1654-1661.*
Munoz-Furlong, Daily Coping Strategies for Patients and Their Families, Pediatrics 2003;111 ;1654-1661.*

* cited by examiner

*Primary Examiner* — Luke Gilligan
*Assistant Examiner* — Tran Nguyen

(57) ABSTRACT

A system includes a Healthcare Advisory System (HAS) module and a server. The HAS module may send user location information to the server. Based on user information and environment information stored on the server, an alert may be generated and sent to a user via the HAS module.

10 Claims, 6 Drawing Sheets

SYSTEM AND METHOD FOR HEALTHCARE ADVISORY SYSTEM

BACKGROUND

People suffering from certain diseases generally need to make certain lifestyle changes in order to maintain their independent lifestyles and to ease the strain on the healthcare system in coping with an increasing number of patients. Lifestyle changes, however, can often be difficult to make.

DETAILED DESCRIPTION OF PREFERRED EMBODIMENTS

The following detailed description of implementations consistent with principles of the invention refers to the accompanying drawings. The same reference numbers in different drawings may identify the same or similar elements. Also, the following detailed description does not limit the invention. Instead, the scope of the invention is defined by the appended claims and their equivalents.

Implementations described herein relate to generating and sending alerts to users. In one implementation, the alerts may be part of a Healthcare Advisory System (HAS).

Figure 1:
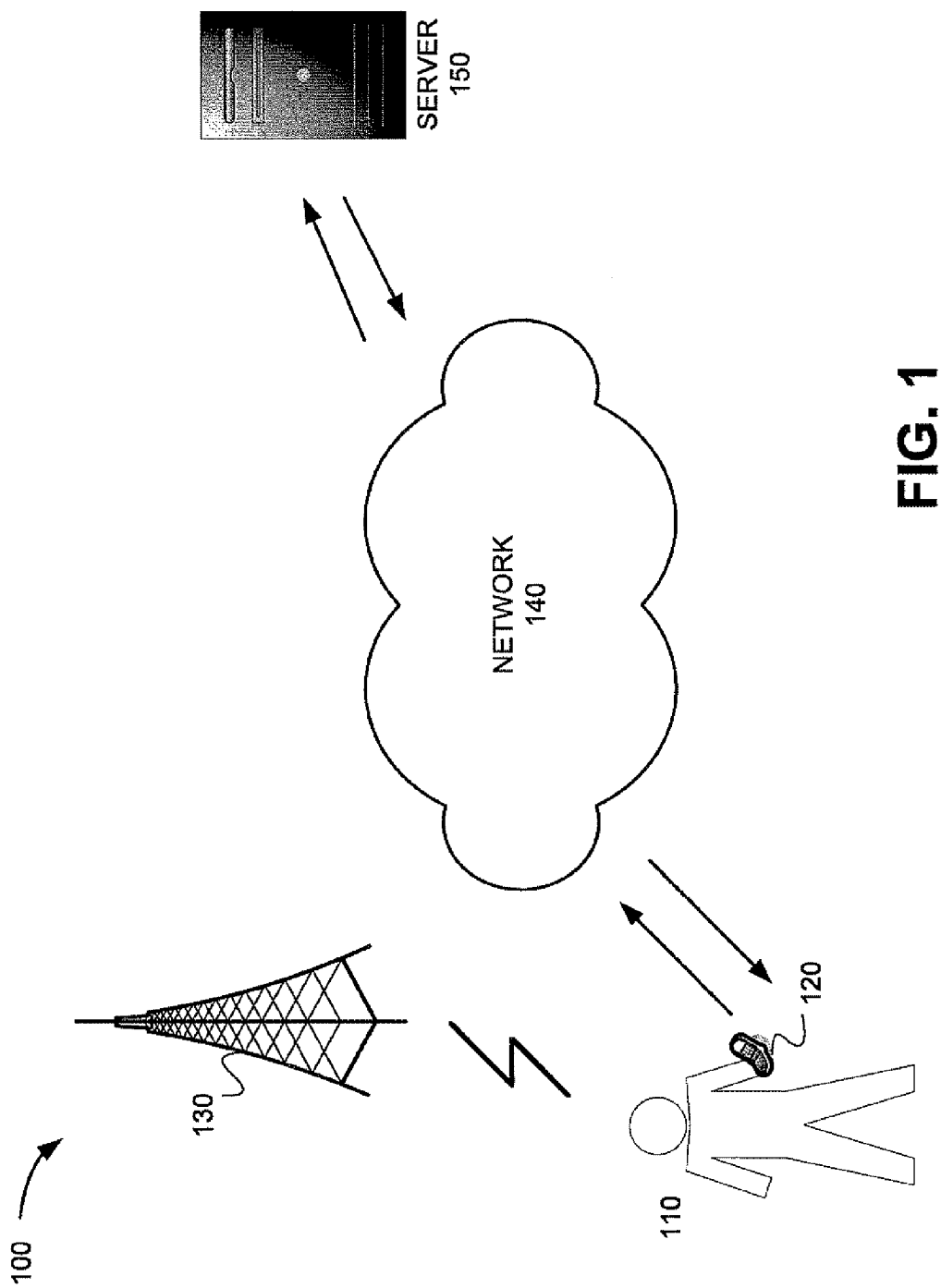
FIG. 1 illustrates an exemplary overview of implementations consistent with principles described herein.

FIG. 1 illustrates an exemplary system 100 in which concepts described herein may be implemented. System 100 may include user 110 carrying mobile HAS module 120, base station 130, network 140, and server 150. It should be understood that system 100 may include other numbers of users, HAS modules, base stations, and servers.

The methods and systems described herein may be implemented in the context of a HAS module such as HAS module 120. As used herein, the term "HAS module" may include a cellular radiotelephone with a multi-line display; a Personal Communications System (PCS) terminal that may combine a cellular radiotelephone with data processing, facsimile and data communications capabilities; a personal digital assistant (PDA) that can include a radiotelephone, pager, Internet/Intranet access, Web browser, organizer, calendar and/or a global positioning system (GPS) receiver, a radio (AM/FM) receiver; and a laptop and/or palmtop receiver or other appliance that includes a radiotelephone transceiver. HAS modules may also be referred to as "pervasive computing" devices that are capable of communicating with other devices via Short Messaging Service (SMS) protocols or other protocols that allow for simultaneous communications of voice, data, music and video information.

Network 140 may include one or more networks including a cellular network, such as a Global System for Mobile communications (GSM) network, a satellite network, the Internet, a telephone network, such as the Public Switched Telephone Network (PSTN), a metropolitan area network (MAN), a wide area network (WAN), a local area network (LAN), or a WiMAX network. HAS module 120 may communicate with server 150 over network 140 via wired, wireless or optical connections. HAS module 120 may incorporate cellular as well as WiFi functionality, WiFi & WiMAX functionality, or some other combination.

In an exemplary implementation, network 140 may include a cellular network used for transmitting data and messages between HAS module 120 and server 150. For example, components of a cellular network may include base station antennas (not shown) that transmit and receive data from mobile terminals within their vicinity. Other components of a cellular network, for example, may also include base stations 130 that connect to the base station antennas and communicate with other devices, such as switches and routers (not shown) in accordance with known techniques.

Base station 130 may include a communication interface that may include any transceiver-like mechanism and one or more processors or microprocessors enabled by software programs and/or hardware to perform functions, such as location determination. Signals transmitted by base station 130 may be received by HAS module 120, and may be used to calculate the position of HAS module 120.

Server 150 may include one or more processors or microprocessors enabled by software programs to perform functions, such as data storage and transmission, and interfacing with other servers (not shown), HAS module 120, and network 140, for example. Server 150 may also include a data storage memory, such as a random access memory (RAM) or another dynamic storage device that stores information related to patient records and environment information, as described below.

Figure 2:
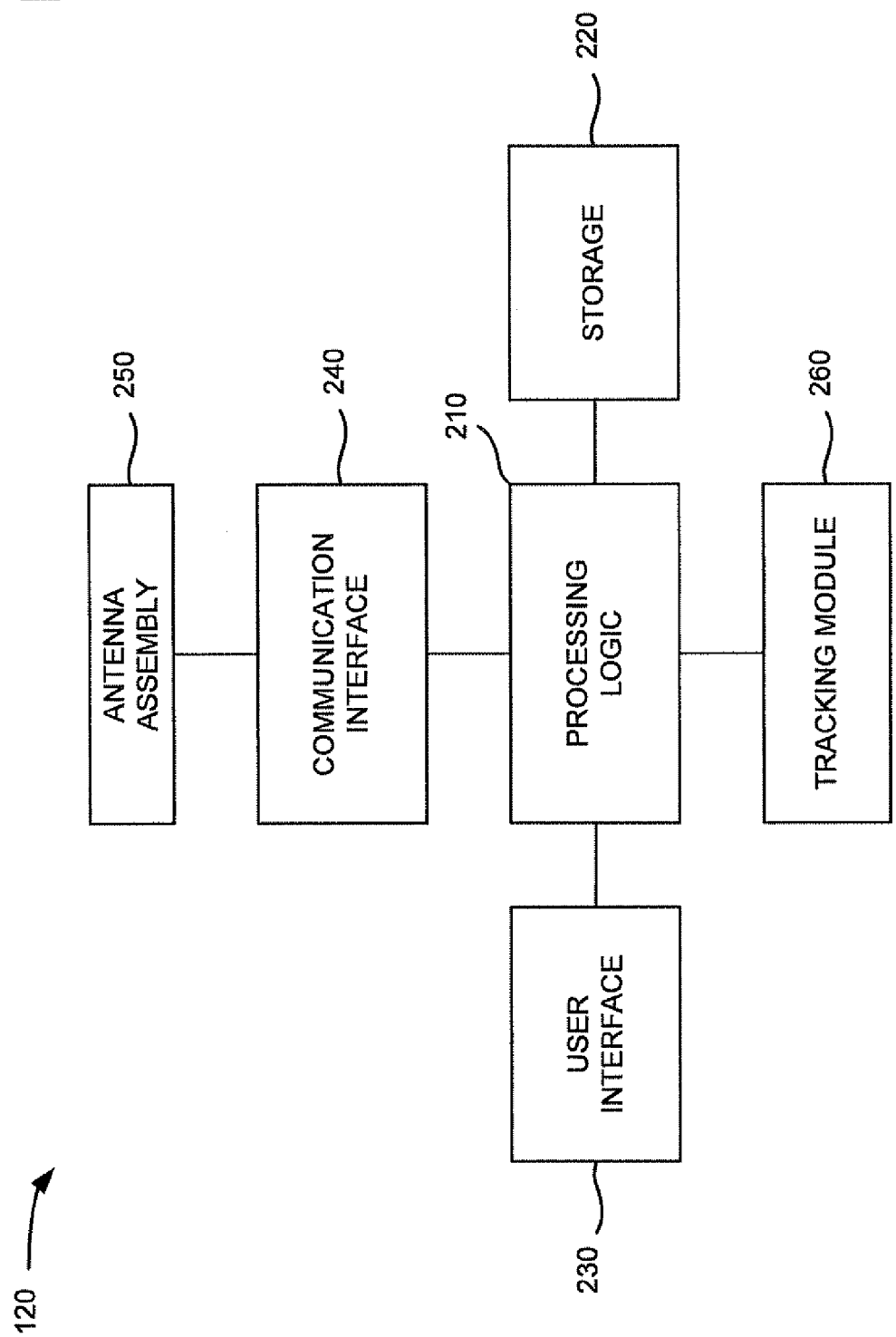
FIG. 2 illustrates an exemplary configuration of the user device of FIG. 1.

FIG. 2 is a diagram of exemplary components of HAS module 120. As shown in FIG. 2, HAS module 120 may include processing logic 210, storage 220, user interface 230, communication interface 240, antenna assembly 250, and tracking module 260. Processing logic 210 may include a processor, microprocessor, an application specific integrated circuit (ASIC), field programmable gate array (FPGA), or the like. Processing logic 210 may include data structures or software programs to control operation of HAS module 120 and its components. Storage 220 may include a random access memory (RAM), a read only memory (ROM), and/or another type of memory to store data and instructions that may be used by processing logic 210.

User interface 230 may include mechanisms for inputting information to HAS module 120 and/or for outputting information from HAS module 120. Examples of input and output mechanisms might include a speaker to receive electrical signals and output audio signals, a microphone to receive audio signals and output electrical signals, control buttons and/or keys on a keypad to permit data and control commands to be input into HAS module 120, and a display to output visual information.

Communication interface 240 may include, for example, a transmitter that may convert baseband signals from processing logic 210 to radio frequency (RF) signals and/or a receiver that may convert RF signals to baseband signals. Alternatively, communication interface 240 may include a transceiver to perform functions of both a transmitter and a receiver. Communication interface 240 may connect to antenna assembly 250 for transmission and reception of the RF signals. Communication interface 240 may also be configured to receive and process signals from base station 130, for example. Antenna assembly 250 may include one or more antennas to transmit and receive RF signals and GPS signals over the air. Antenna assembly 250 may receive RF signals from communication interface 240 and transmit them over the air and receive RF signals over the air and provide them to communication interface 240.

Tracking module 260 may contain hardware and/or software for receiving and processing signals from base station 130 or GPS signals in order to calculate a position of HAS module 120.

As will be described in detail below, HAS module 120 may perform operations in response to processing logic 210 executing software instructions to display and transmit/receive messages to/from a server, using an application contained in a computer-readable medium, such as storage 220. A computer-readable medium may be defined as a physical or logical memory device and/or carrier wave.

The software instructions may be read into storage 220 from another computer-readable medium or from another device via communication interface 240. The software instructions contained in storage 220 may cause processing logic 210 to perform processes that will be described later. Alternatively, hardwired circuitry may be used in place of or in combination with software instructions to implement processes consistent with the embodiments. Thus, implementations consistent with the principles of the embodiments are not limited to any specific combination of hardware circuitry and software.

Figure 3:
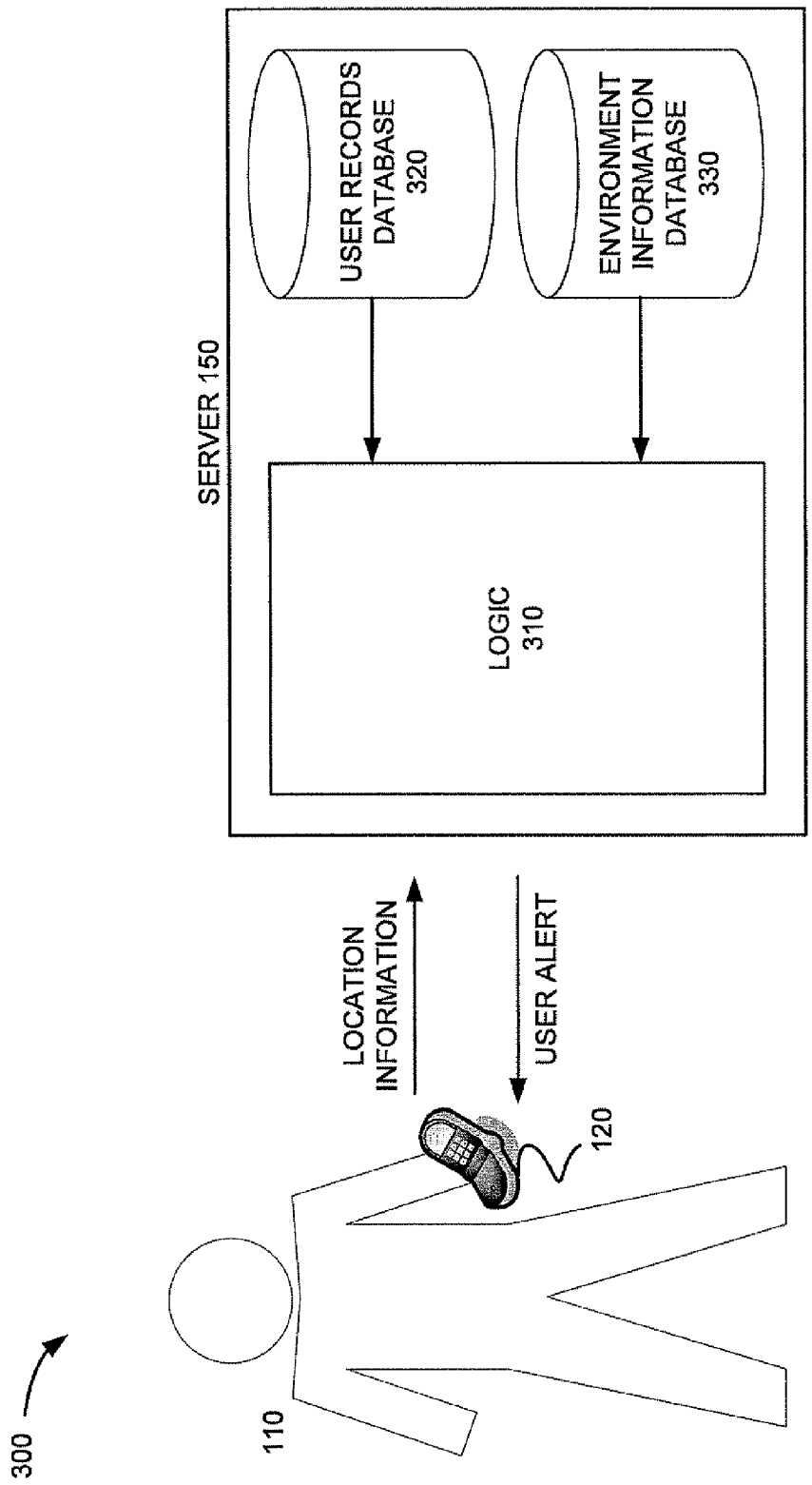
FIG. 3 illustrates an exemplary functional block diagram of a Healthcare Advisory System (HAS)

FIG. 3 is a functional block diagram of an exemplary HAS. System 300 may include user 110 carrying HAS module 120 and server 150. Server 150 may include logic 310, user records database 320, and environment information database 330.

User records database 320 may include information relating to users of system 300. In one implementation, the information may relate to healthcare of the user and may include, for example, user condition information and user treatment information. For example, if a user is suffering from diabetes, user records database 320 may include information about the severity of the diabetes, what medication the user is taking, how frequently the user is taking the medication, and information about what food the user can and cannot eat.

Environment information database 330 may include information about a user's surroundings. For example, environment information database 330 may include information about structures such as restaurants, bathrooms, police and fire stations, and hospitals in the vicinity of the user. The information in environment database 330 may be mapped to geographic location information so that, for a given geographic location, the environment in the vicinity of that location can be determined.

For example, for a restaurant, environment information database 330 may store menu items offered by the restaurant and the ingredients or nutritional information for the menu items. Environment information database 330 may also store geographical location information ("map data") relating to the restaurant. The map data may also contain the location of other entities that are relevant to the operation of HAS 300, such as police stations, fire stations, or hospitals. Information other than restaurant menu information or location information may additionally be stored by environment information database 330. In general, any information related to the environment that a user is likely to interact with and which may be relevant for providing healthcare advisory alerts may be stored in environment information database 330. As a further example, weather information or the locations of bathrooms within buildings may be stored by environment information database 330.

Information "stored" by environment information database 330, as this term is used herein, is intended to include information that environment information database 330 may dynamically access from other sources. For example, weather information and nutritional information relating to items on a restaurant's menu may be accessed from other severs on network 140 as the information is needed by HAS 300.

HAS module 120 may send location information (i.e. information identifying where the user is located) to server 150. For example, HAS module 120 may send the location information periodically or at the request of user 110. Server 150 may access user records database 320 to determine, for example, the user's medical condition and possible treatment options. Server 150 may also access environment information database 330 to determine information about user 10's surroundings based on the location information. Information from user records database 320 and environment information database 330 may be sent to logic 310. Logic 310 may analyze the environment information and the information about the surroundings of the user and determine if a healthcare alert should be generated. If appropriate, logic 310 may generate an alert. Server 150 may then send the alert to HAS module 120 via network 140.

Figure 4:
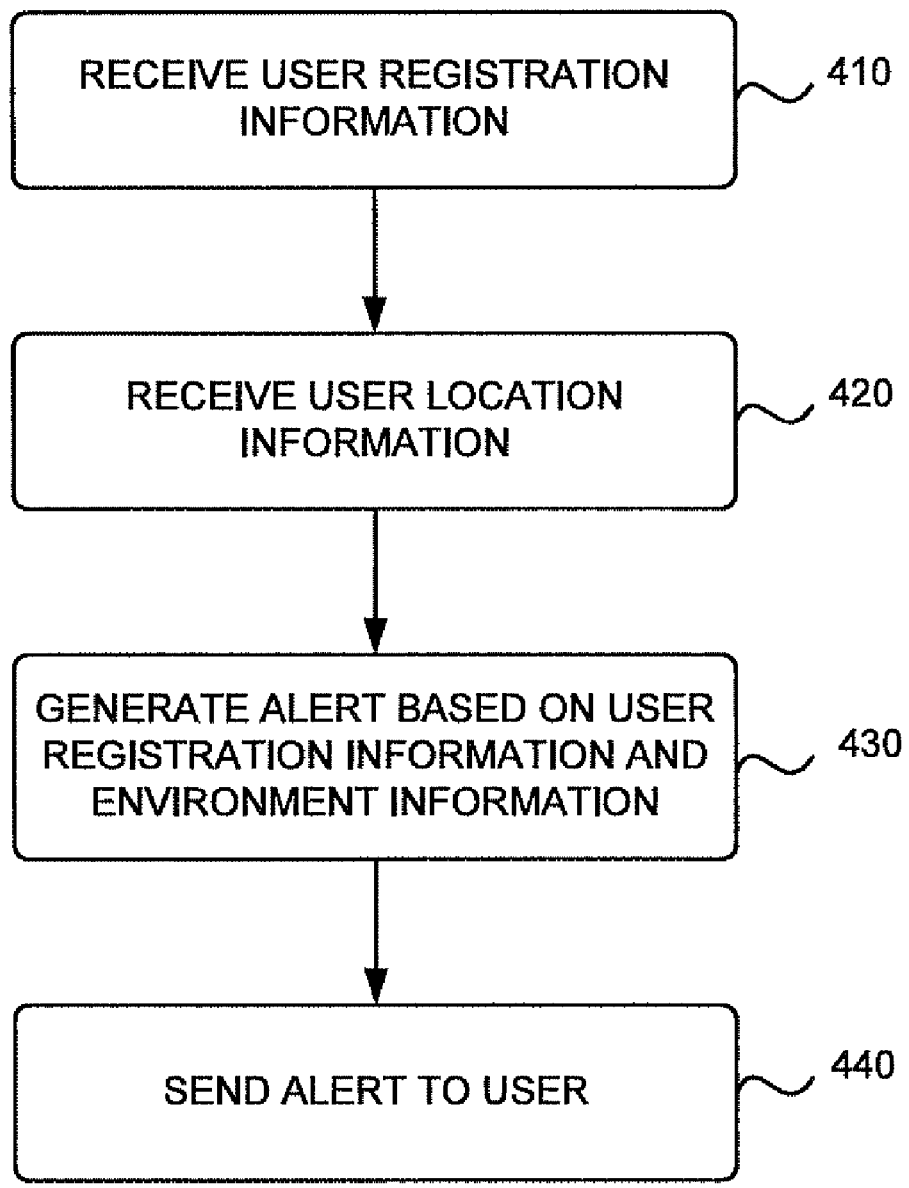
FIG. 4 illustrates a flow chart of exemplary processing for sending users alerts.

FIG. 4 illustrates a flow chart of exemplary processing for generating and sending a user alert. Processing may begin with the one-time receipt of user registration information (block 410). User registration information may include, for example, user name, address, billing information, user condition information, and user treatment information. Other information may also be included in the user registration information. This information may be stored in user records database 320 of server 150.

In one implementation, the user registration information may be selected by the user. For example, when the user (or the user's doctor) registers to receive alerts, the user may select specific types of alerts to receive. For example, a user may register to receive alerts about nutritional information, weather, allergen information, etc. The system may also automatically generate possible types of alerts based on the user's medical information. For example, if a user with diabetes registers to receive alerts about nutritional information in restaurants, the system may also send the user alerts about sale items on nutritious foods when the user is at the supermarket. The user may also register to receive custom alerts. For example, a user may wish to receive an alert when the user is outside and the UV index is above a certain threshold.

Server 150 may receive the location of user 110 based upon the location of HAS module 120 (block 420). The location of HAS module 120 may be determined by base station 130, a GPS tracking device, or any other location monitoring system. The location of HAS module 120 may be determined when HAS module 120 is indoors or outdoors. HAS module 120 may send the location information to server 150 via network 140.

Based on user registration information and environment information, logic 110 may determine whether an alert should be generated (block 430). For example, when server 150 receives the location information from HAS module 120, logic 310 may retrieve information about user 110's surroundings from environment information database 330. Server logic 310 may also retrieve information about user 110 from user records database 320. Based on this information, logic 310 may generate an alert for user 110 (block 430).

Logic 310 may generate an alert when it is determined that the user may benefit from a health alert. This determination may be based on, for example, the time of day. For example, if a user is required to take medication three times a day, logic 310 may generate a reminder alert at three pre-set times during the day.

The determination may also be based upon the location of a user. For example, assume a user is suffering from a urinary tract infection (as a result of a sexually-transmitted disease, for instance) and has been told to routinely check the color of his or her urine. In this case, logic 310 may generate a reminder alert whenever it is determined that the user is in the restroom.

Logic 310 may also generate alerts based on a user request. For example, if a user goes out one day, gets lost, and is in need of assistance home, the user may request an alert giving directions home or showing a map of the area.

Finally, server 150 may send the user alert to user 110 via HAS module 120 (block 440). The alert may be, for example, visual (e.g. text message, graphic, map) or audio (e.g. voice based).

Figure 5:
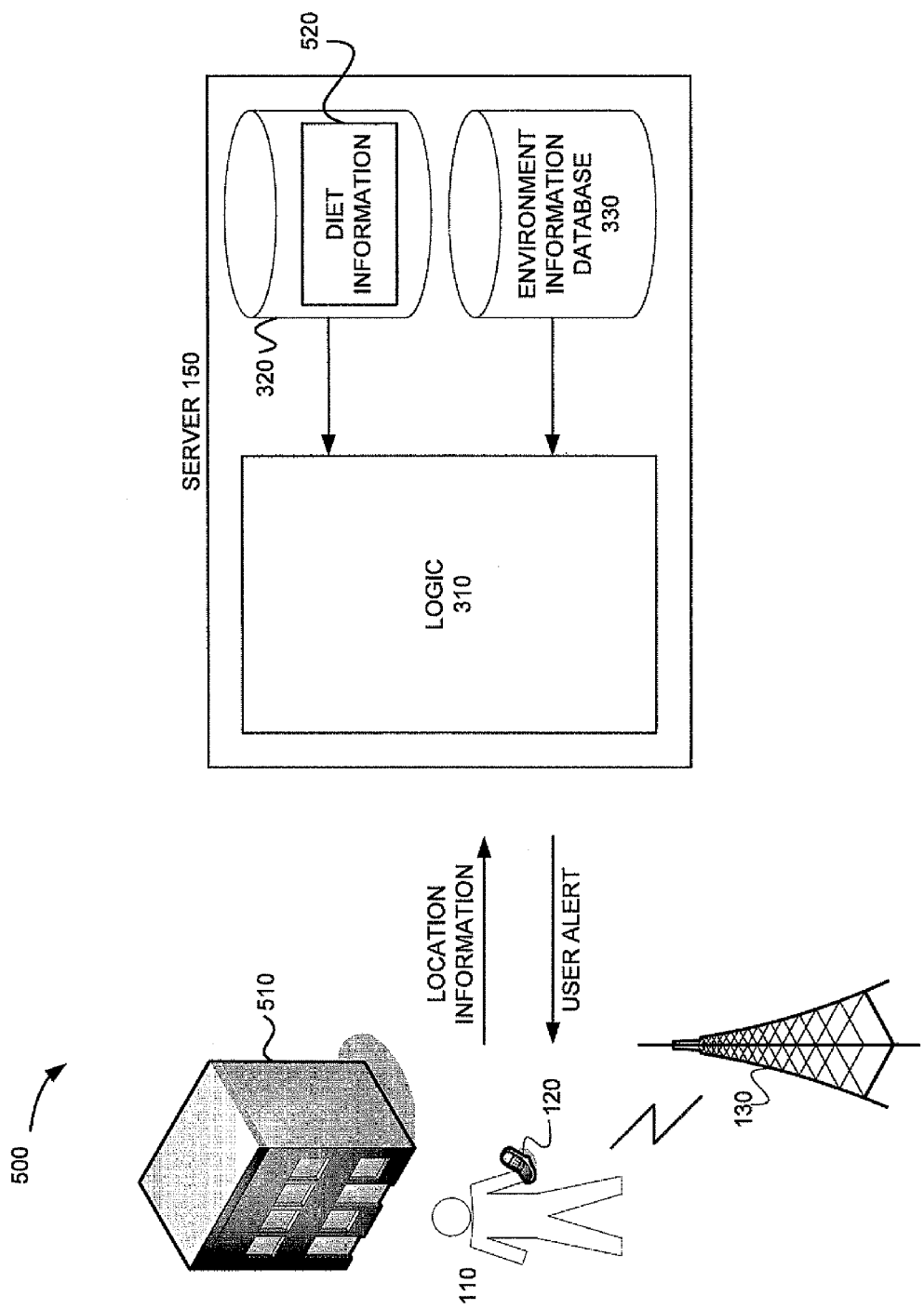
FIGS. 5 and 6 illustrate examples of the processing described with respect to FIG. 4.
Figure 6:
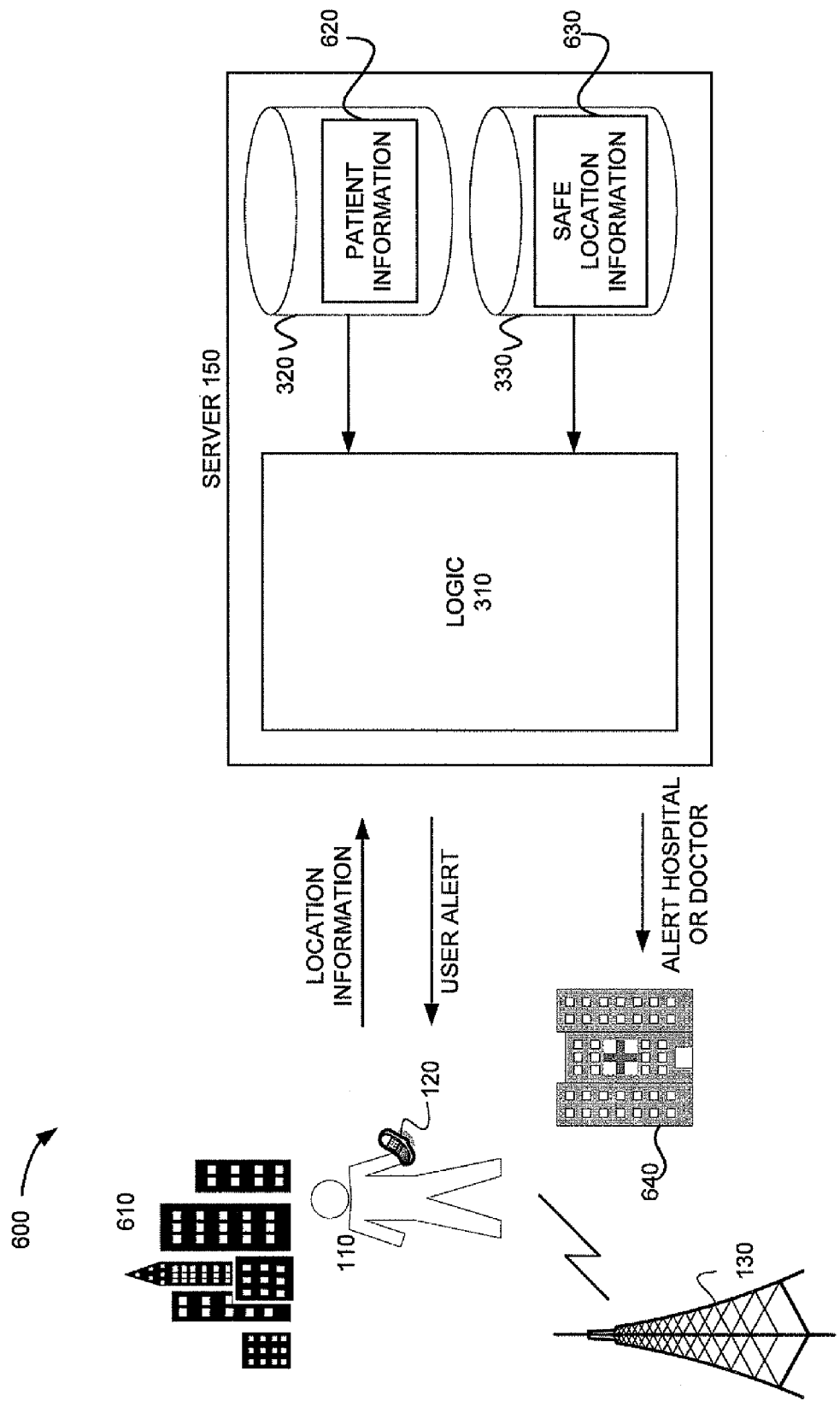

The following examples illustrate the processing described above with respect to FIG. 4. FIG. 5 is a diagram conceptually illustrating a first example system 500 and FIG. 6 is a diagram conceptually illustrating a second example system 600.

In a first example 500, assume user 110 suffers from a severe case of diabetes and therefore may have to be reminded to avoid certain foods. User 110 may enter restaurant 510 with HAS module 120. Location information may be sent to server 150, which may search environment information database 330 to determine that user 110 is near restaurant 510. Based on this information, server 150 may query environment database 330 to determine menu information. The menu information and user diet information 520 from user records database 320 may be sent to logic 310. Logic 310 may analyze restaurant 510's menu and generate, based on diet information 520, a list of items on the menu that user 110 can order (or, alternatively, a list of items the user should avoid). This information may then be sent to HAS module 120 as an alert.

In a second example 600, assume user 110 suffers from Alzheimer's disease or glaucoma. Further, assume user 110 goes out one day, gets disoriented, and needs assistance getting home. The user may then request assistance through HAS module 120. The location of HAS module 120 may be determined and sent to server 150 via network 140. Based upon the location information, environment information database 330 may be searched to determine user 110's surroundings and information about the surroundings may be sent to server logic 310. Information about the surroundings may include, for example, safe location information 630 (e.g. location of local police stations, fire stations, or hospitals), or directions to the home of user 110. Patient information 620 from user records database 320 may also be sent to logic 310 and an alert may be generated based on patient information 620 and location information 630. For example, if, based on patient information 620, it is determined that user 110 has adequate mental facilities, an alert may be generated including directions that will lead the user home. If, however, user 110's disease is at a more advanced stage, an alert may be generated giving user 110 instructions to stay calm and a separate alert may be generated to a person responsible for the user, the police, or a hospital, collectively illustrated as entity 640. The alerts may then be sent to user 110 via HAS module 120 and to entity 640. In one implementation, the alert may be implemented as a voice-based interface that may speak to user 110 in a familiar voice.

Implementations described herein provide alerts to users of a Healthcare Advisory System (HAS). User location information may be determined based upon the location of a mobile HAS module. Alerts are generated based upon user information and environment information determined based upon the user location information and sent to the user via the mobile HAS module.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

For example, while a series of acts has been described above with respect to FIG. 4, the order of the acts may differ in other implementations consistent with principles of the invention. Moreover, non-dependent acts may be performed in parallel.

It will be apparent that aspects of the embodiments, as described above, may be implemented in many different forms of software, firmware, and hardware in the implementations illustrated in the figures. The actual software code or specialized control hardware used to implement these embodiments consistent with the principles of the invention is not limiting of the invention. Thus, the operation and behavior of the preferred embodiments of the invention were described without reference to the specific software code—it being understood that software and control hardware may be designed to implement the embodiments based on the description herein.

Further, certain portions of the invention may be implemented as "logic" that performs one or more functions. This logic may include hardware, such as an application specific integrated circuit, a field programmable gate array, a processor, or a microprocessor, software, or a combination of hardware and software.

No element, act, or instruction used in the description of the present application should be construed as critical or essential to the invention unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. An automated method performed by a server device in communication with a mobile device, comprising:
    populating a first database with health-related information associated with a user of the mobile device;
    populating a second database with information relating to building structures in different geographic locations;
    receiving, by a processor of the server device and from the mobile device, information identifying a geographic location of the user;
    accessing, by the processor of the server device and in response to receiving the information identifying the geographic location of the user, the first database to identify the health-related information associated with the user;
    accessing, by the processor of the server device and in response to receiving the information identifying the geographic location of the user, the second database to identify information relating to one or more building structures in a vicinity of the geographic location of the user, where the information relating to the one or more building structures includes nutritional information associated with menu items of a restaurant;
    determining, by the processor of the server device, that a health-related condition exists based on the health-related information and the identified information relating to one or more building structures;

generating, by the processor of the server device, an alert relating to the health-related condition, where the alert includes one more menu items of the menu items of the restaurant; and transmitting, by the processor of the server device, the alert to the mobile device associated with the user.

2. The method of claim 1, further comprising:

sending the alert to a second user.

3. The method of claim 2, where the second user includes a physician of the user.

4. The method of claim 1, where the health-related information includes a medical condition of the user.

5. The method of claim 1, where the information relating to the building structures includes a map.

6. The method of claim 1, where transmitting the alert includes transmitting the alert to a mobile terminal associated with a user that is different than the user.

7. The method of claim 1, where the alert includes a text message.

8. A system comprising:

a first database, stored on a server device, populated with health-related information associated with a user of a mobile device;

a second database, stored on the server device, populated with information relating to building structures in different geographic locations;

the server device to:

receive information identifying a geographic location of the user;

access, in response to receiving the information identifying the geographic location of the user, the first database to identify the health-related information associated with the user;

access, in response to receiving the information identifying the geographic location of the user, the second database to identify information relating to one or more building structures in a vicinity of the geographic location of the user, where the information relating to the one or more building structures includes nutritional information associated with menu items of a restaurant;

determine that a health-related condition exists based on the health-related information and the identified information relating to one or more building structures;

generate an alert relating to the health-related condition, where the alert includes one more menu items of the menu items of the restaurant; and transmit the alert to the mobile device associated with the user.

9. The system of claim 8, where the server device is further to:

send an alert to a second user responsible for care of the user.

10. The system of claim 8, where the information relating to the building structures includes a map.

* * * * *